United States Patent
Jain et al.

(10) Patent No.: US 6,337,095 B1
(45) Date of Patent: Jan. 8, 2002

(54) PROCESS FOR THE ISOLATION OF COMPOUND SCOPOLETIN USEFUL AS NITRIC OXIDE SYNTHESIS INHIBITOR

(75) Inventors: Dharam Chand Jain; Neerja Pant; Madan Mohan Gupta; Rajendra Singh Bhakuni; Ram Kishor Verma; Sudeep Tandon; Shiv Kumar Gupta; Amit Tewari; Atul Prakash Kahol; Sushil Kumar, all of Lucknow (IN)

(73) Assignee: Council of Scientific and Industrial Research, New Dehli (IN)

( * ) Notice: Subject to any disclaimer, the term of this patent is extended or adjusted under 35 U.S.C. 154(b) by 0 days.

(21) Appl. No.: 09/538,893

(22) Filed: Mar. 30, 2000

(51) Int. Cl.⁷ .......................... A01N 65/00; A61K 35/78
(52) U.S. Cl. ...................... 424/740; 424/774; 424/773; 424/779; 424/725
(58) Field of Search .............................. 424/195.1, 725, 424/779, 740, 774, 773

(56) References Cited

U.S. PATENT DOCUMENTS 5,989,556 A * 11/1999 Tsai et al. ................. 424/195.1

OTHER PUBLICATIONS

Al–Hazimi et al. A p–Coumaric Acid Ester and Flavonoids from Artemisia Monosperma; Oriental J. Chem., vol. 8, No. 3 pp. 203–207, 1992.*

Kery et al. Isolation of Scopoletin in Gundelia Tourneforthii by DCCC; Fitoterapia, vol. LVI, No. 1, pp. 42–44, 1985.*

Martinez et al. Phenolic and Acetylenic Metabolites from Artemisia Assonana; Phytochemistry, vol. 26, No. 9, pp. 2619–2624, 1987.*

Vasconcelos et al. Chromones and Flavones from Artemisia Campestris Subsp. M Artima; Phytochemistry, vol. 49, No. 5, pp. 1421–1424, 1998.*

Zhang et al. HPLC Determination of Five Constituents in Plants of Genus Ligusticum; ACTA Pharmaceutica Sinica, vol. 31, No. 8, English Abstract, 1996.*

* cited by examiner

*Primary Examiner*—Jon P. Weber
*Assistant Examiner*—Patricia Patten
(74) *Attorney, Agent, or Firm*—Merchant & Gould P.C.

(57) ABSTRACT

The invention relates to a process for the isolation of compound scopoletin which is used as nitric oxide synthesis inhibitor from *Artemisia annua* and other plant families, said process comprising extraction of dried powdered material of different plant parts with an aqueous acetonitrite solvent in the ratio of 1:5 for 6 to 8 hrs., concentration of the extracted solvent upto 30% of its original extract under vacuum, partitioning the concentrated extract with halogenated solvent to transfer scopoletin in the non-polar halogenated solvent, drying halogenated solvent over anhydrous sodium sulphate and evaporating the solvent, crystallizing the residues in methanol and filtering the crystals, concentrating the filtrate and chromatographed on silica gel, eluting scopoletin in chloroform methanol mixture; and crystallization of the fractions containing the scopoletin to get the pure scopoletin compound.

9 Claims, No Drawings

PROCESS FOR THE ISOLATION OF COMPOUND SCOPOLETIN USEFUL AS NITRIC OXIDE SYNTHESIS INHIBITOR

FIELD OF INVENTION

The present invention relates to a process for the isolation of compound scopoletin useful as a nitric oxide synthesis inhibitor from the plant *Artemisia annua* and other plant families. Scopoletin belongs to the coumarin group of compounds. Scopoletin (7-hydroxy-6-methoxy coumarin is a derivative of benzo-α-pyrone coumarin and is found in plants both in the free state and glycosides.

BACKGROUND OF INVENTION

Natural coumarins exert varied and pronounced effects on living organisms. Coumarins exhibit numerous pharmalogical and physiological activities such as antibacterial, vasoditory and diuretic effects, anticoagulant properties, hepatoprotective and respiratory stimulation. Scopoletin showed very good growth inhibitory properties. (Shilling D G and Yoshikawa F, *Amerchem. Soc. Syinp Series*, 330:335–342). Recently, it was reported that scopoletin showed inhibition of nitric oxide (NO) synthesis in murine macrophages. Macrophages play a major role in last defense against infection and tumor development and this activity is regulated through the production of several mediates. The production of NO by macrophages mediates killing or growth inhibitors of tumor cells, bacteria fungi and parasites. Therefore it will be valuable to develop a potent and economic source of scopoletin, inhibitor of NO for potential therapeutic and commercial use in the future (Tai-Hyun Kang et al: scopoletin: an inducible NO synthesis inhibitory active constituents from *Artemisia feddi, Planta Medica*, 65:400–403, 1999); Invitro inducible NO synthesis inhibitory active constituent from *Ttraxinus rhynchobhyeli*, Plant Medica, 65:656–658, 1999).

Scopoletin is widely distributed in the plant kingdom and is isolated from the different parts (roots, fruits, leaves, stems, etc.) of the plant, but several related members frequently are found together making their isolation difficult. In general isolation of coumarins depends initially upon successive extraction of dried plant with commonly used solvents of increasing polarities (pet ether, benzene, ether, acetone or methanol).

The conventional method used for the isolation of the coumarins used dried powder material extracted with 95% methanol/ethanol, and the concentrated extract was treated with 10% alkali solution. The alkaline solution was extracted with ether to remove the fatty material. The aqueous solution was acidified and extracted with ether or chloroform to obtain crude coumarins. Further, the purification was carried out on column chromatography over silica gel or alumina to get pure coumarins. Certain coumarins (e.g. umbilliferon, scopoletin) can be isolated from plant tissues by sublimation methods (Abu-Mustafa, E. A.; El-Tawil, B. A. H. and M. B. E. Fayez; Phytochemistry, 3, 701 (1964)).

However, the method of isolation of coumarin through acid based treatment is not ideal because it is hardly possible to avoid some degradation of the coumarins which lead to the isolation of artefacts rather than the original compound or the loss of the compounds. In another process purification done by sublimation may involve thermal degradation with formation of artefacts. The overall yield of recovery is reduced. As such no plant with high content of scopoletin for commercial exploitation nor any large scale process for the isolation of scopoletin has been reported.

OBJECTS OF THE INVENTION

The objective of the present invention is to explore new plant/plant part with a high content of scopoletin.

Another objective of the invention is the selection of solvent for the selective extraction of scopoletin.

Still another objective of the invention is to develop an economic process for the isolation of pure scopoletin.

SUMMARY OF THE INVENTION

Accordingly, the present invention provides a process for the isolation of nitric oxide synthesis inhibitor compound scopoletin from the plant *Artemisia annua*, and other plant families, which comprises the extracting the powder plant parts with an aqueous acetonitrile solvent, partitioning with a chlorinated solvent, evaporating the solvent, crystallizing a residue from the solvent and employing chromatography to yield pure scopoletin.

Novelty of the Process
1. Selection of the plant part for the extraction of scopoletin improved the yield and reduced the processing cost.
2. The extraction of the plant part with aqueous acetonitrile is more economic with a better yield of scopoletin as compared to the use of other polar solvents like methanol or ethanol.
3. In this process, by avoiding any acid base treatment for the isolation of scopoletin the yield was improved.
4. The selective transfer of scopoletin from the aqueous extract to the halogentaed non polar phase resulted in easy purfication and isolation of pure scopoletin.
5. The purificaton of the crude extract resulting in crystallisation of 50% of scopoletin before the chromatography.
6. The process allows the reuse of solvents and silica gel.
7. These advantages are of significant economic values for large scale production of scopoletin.

DETAILED DESCRIPTION OF THE INVENTION

The present invention provides a process for the isolation of compound scopoletin which is used as nitric oxide synthesis inhibitor from *Artemisia annua* and other plant families, said process comprising:

a) extraction of dried powdered material of different plant parts with an aqueous acetonitrile solvent in the ratio of 1:5 for 6 to 8 hrs., b) concentration of the extracted solvent upto 30% of its original extract under vacuum, c) partitioning the concentrated extract with halogenated solvent to transfer scopoletin in the non-polar halogenated solvent, d) drying halogenated solvent over anhydrous sodium sulphate and evaporating the solvent, e) crystallizing the residues in methanol and filtering the crystals, f) concentrating the filtrate and chromatographed on silica gel, g) eluting scopoletin in chloroform methanol mixture; and crystallization of the fractions containing the scopoletin to get the pure scopoletin compound.

In one embodiment of the invention, *Artemisia annua* plant was selected for the isolation of scopoletin. *Artemisia annua* ariel parts from Spain have reported 0.02% scopoletin and England (cult) 0.034%. China has also reported the presence of scopoletin from the whole plant (Brown, G. D.: Two new compounds from *Artemisia annua*: J.Nat. Prod. 58, 300 (1992); Marco, J. A.; Sawz, J. F.; Bea, J. F.; Barber, O.: Phenolic constituents from *Artemisia annua*: Pharmazie 45, 382–383 (1990); Liu, H. M.; Li, G. L., Wu, H. Z.: Studies on the constituents of Quinghao:Yao Hsuch Hsuch Pao, 37, 129–143 (1979)).

In India CIMAP, Lucknow, has developed a new variety of *Artemisia annua* "Jeevan raksha" producing high content of artemisinin and biomass (stems & leaves). Artemisinin and its derivative are reported as potent against chloroquine resistant multi drug resistant and severe complicated malaria. *Artemisia annua* plant is the only source of artemisinin.

Screening of all the three major parts of the *A. annua* plant of the new variety for scopoletin was carried out by HPLC. The content of scopoletin obtained in different plant parts are as follows; leaves 0.2%, Stems 0.3% and roots 0.004%. The yield of the scopoletin is very high as compared to other reported plants. The stem part of the plant *Artemisia annua* is a waste material as no artemisinin is present in the stems. The biomass of the stem portion of the plant is five times more than of the leaves. Therefore, we have selected the stem part of the plant *Artemisia annua* for the isolation of scopoletin. Also the stem portion of the stems was found to contain less colouring and fatty material which eases the isolation and purification of scopoletin.

In the prior art, it has been observed that non polar solvents for extraction of the plant materials were employed, resulting in less recovery of coumarins. Still, polar solvents (methanol and ethanol) used for the extraction of coumarins resulted in a higher amount of total extract having more colouring and fatty material. The separation of fatty and colouring matter is a difficult task. In the present invention, we have selected aqueous acetonitrile solvent for the extraction which yielded a higher amount of scopoletin with less amount of colouring and fatty material. Also, the separation of water from acetonitrile for recovery of the pure solvent for reuse is much easier.

In the prior art the scopoletin was purified from the crude extract through acid base treatment or by sublimation method which reduces the amount of scopoletin due to rearrangements and thermal decomposition. In the present invention of the improved process, selective transfer of the coumarins from the aqueous extract into the non polar phase was carried out by partitioning the aqueous phase with chlorinated solvent (Carbon tetra chloride, di chloromethane, chloroform). By employing this step, most of the colouring and fatty material is left in the polar phase thereby enriching the scopoletin in the non polar phase which is easily crystallisable (50–60%) in the crude extract itself The scopoletin left in the mother liquor after crystallization is subjected to column chromatography over silica gel in ratio of only 1:10 for complete isolation of the pure scopoletin. The partition of scopoletin from aqueous extract to non polar solvent reduces the bulkiness of the crude extract by 60–70% which in terms requires less amount of silica gel and solvent in the process.

The process consists of the following operations
1. Shade drying and grinding of the stems of *Artemisia annua*.
2. Extracting the powdered *Artemisia annua* stems with aqueous acetonitrile solvent by cold percolation.
3. Concentrating the total extract under vacuum.
4. Partitioning of the aqueous acetonitrile phase with halogenated solvent.
5. Removal of moisture from the total halogenated extract.
6. Distillation of the halogenated solvent for obtaining the residual extract.
7. Crystallisation of the scopoletin from the residual extract.
8. Filtration and concentration of mother liquor.
9. Column Chromatography of mother liquor over silica gel for recovery of pure scopoletin.

The present invention is to provide a process for the extraction and isolation of scopoletin from the plant *Artemisia annua* to overcome the drawbacks of the hitherto known process. The invention more particularly provides a process which gives a cheaper and higher yield of nitric oxide synthesis inhibitor compound scopoletin from the natural source.

Accordingly, the present invention provides a process for the extraction and isolation of scopoletin from *Artemisia annua* which comprises extraction of a plant part, preferably dried stem powder of *Artemisia annua* with aqueous acetonitrile solvent in the ratio of 1:5, concentration of the extract under a vacuum, partitioning of the concentrated extract with a non polar halogenated solvent, distillation of the halogenated solvent, crystallization of the residue in methanol, filtration of scopoletin, concentration of the mother liquor and performing chromatography over silica gel for obtaining pure scopoletin.

In an embodiment, of the invention the solvent used for the extraction is selected in different ratios of acetonitrile-:water from 1:9 to 9:1.

In another embodiment, of the invention the halogenated solvent used for partitioning is to be selected from dichloromethane, carbon tetra chloride, chloroform etc. In another embodiment of the invention the plant part for extraction of scopoletin is selected from stems, leaves, roots etc.

In another embodiment, of the invention the separation of scopoletin over silica gel whereas the ratio of crude extract to silica gel is selected from 1:5 to 1:20 preferably either from 1:5, 1:10 or 1:20.

The details of the invention provided in the following examples are given by way of illustration only should not be construed to limit the scope of the present invention Yet another embodiment of the invention, extraction and isolation of scopoletin is from plant families such as Umbelliferae, Rutaceae, Compositae, Leguminosae, Moraceae, Caryophyllacae, etc.

Still another embodiment of the invention, the scopoletin is crystallized in the solvent which is selected from chloroform, acetone, methanol and mixtures thereof.

One another embodiment of the invention, scopoletin isolated from different parts of *Artemisia annua* is in the range of 0.25–0.30% in stem, 0.16–0.20% in leaves, and 0.003–0.004% in roots.

EXAMPLE 1

Selection of plant parts for extraction

A comparative study of scopoletin content in the different parts of *Artemisia annua* (leaves, stem, root) was done. Dried powdered sample of 0.1 gm was extracted with methanol. The extract was filtered and the solvent was evaporated to dryness. The extract was dissolved in 1 ml methanol. The content of scopoletin in each sample was estimated by LC 8 A Shimadzu HPLC-equipped with photodiode array detector under the following operating conditions: mobile phase acetonitrile; water (30;70); flow rate 0.8 ml/min, detection at 230 nm, colum-C18 Lichrosorb, 10 um Merck Germany. Quantification was performed using a calibration curve of the standard scopoletin prepared as a 1 mg/5 ml solution in methanol. The content of scopoletin estimated in different plant parts are as follows; leaves (0.16), stems (0.2) and root (0.003).

EXAMPLE 2
Selection of solvent for extraction

Stem powered sample (0.1 gm) of *Artemisia annua* was extracted with 10 ml different solvents (dichloromethane, chloroform, ethylacetate, methanol, acetonitrile, water, methanol: water (9:1), ethanol:water (9:1) and acetonitrile-:water (9:1)) for cold percolation for 24 hrs. Each extract was filtered and evaporated under a vacuum. Each extract was dissolved in 1 ml HPLC grade methanol and estimated the scopoletin content by HPLC method as described in example-1. Scopoletin content in stem of *Artemisia annua* recorded in different solvents are as follows; dichloromethane (0.016%), chloroform (0.16%), ethyl acetate (0.09%), methanol (0.2%), ethanol (0.24%), acetonitrile (0.22%), water (0.28%), methanol:water (9;1;0.16%), ethanol:water (9:1;0.23%) and acetonitrile:water (9:1;0.30%).

EXAMPLE 3
Extraction and isolation of scopoletin from stems

*Artemisia annua* stems were ground into powder. The powdered material (100 gm) was extracted with 10% aqueous acetonitrile (5×500 ml) in a percolator for 6–8 hrs. The total extract was concentrated under a vacuum up to 30% of its original quantity. The concentrated aqueous extract was partitioned with chloroform (5×200 ml). The chloroform extract was dried over anhydrous sodium sulphate and the solvent was evaporated to get a 2.0 gm residue. The residue was redissolved in 25 ml methanol and kept for crystallization 4–5 hrs in a refrigerator. The crystalline compound was filtered and dried to get pure scopoletin. The process of crystallization was repeated two times to get 60% of a purified compound. The remaining scopoletin in filtrate was isolated by column chromatography over silica gel in the ratio of (1:20) and the scopoletin was eluted with 4% methanol in chloroform. The scopoletin containing fractions were evaporated and subjected to crystallization, which afforded pure scopoletin. Thereby (85%) of pure scopoletin was isolated from 100 gms of stem powder of 0.3% scopoletin content. The scopoletin was identified by mp, IR, $^1$H, $^{13}$C NMR and mass spectral data, as reported in the literature.

EXAMPLE 4
Extraction and isolation of scopoletin from stems

*Artemisia annua* stems were ground into powder. The powdered material (100 gm) was extracted with 30% aqueous acetonitrile (5×500 ml) in a percolator for 6–8 hrs. The total extract was concentrated under a vacuum up to 30% of its original quantity. The concentrated aqueous extract was partitioned with chloroform (5×200 ml). The chloroform extract was dried over anhydrous sodium sulphate and the solvent was evaporated to get a 2.0 gm residue. The residue was redissolved in 25 ml methanol and kept for crystallization 4–5 hrs in a refrigerator. The crystalline compound was filtered and dried to get pure scopoletin. The process of crystallization was repeated two times to get 50% of a purified compound. The remaining scopoletin in filtrate was isolated by column chromatography over silica gel in the ratio of (1:10) and the scopoletin was eluted with 2% methanol in chloroform. The scopoletin containing fractions were evaporated and subjected to crystallization, which afforded pure scopoletin. Thereby (82%) of pure scopoletin was isolated from 100 gms of stem powder of 0.3% scopoletin content.

EXAMPLE 5
Extraction and isolation of scopoletin from stems

*Artemisia annua* stems were ground into powder. The powdered material (100 gm) was extracted with 70% aqueous acetonitrile (5×500 ml) in a percolator for 6–8 hrs. The total extract was concentrated under a vacuum up to 30% of its original quantity. The concentrated aqueous extract was partitioned with chloroform (5×200 ml). The chloroform extract was dried over anhydrous sodium sulphate and the solvent was evaporated to get a 2.30 gm residue. The residue was redissolved in 25 ml methanol and kept for crystallization 4–5 hrs in a refrigerator. The crystalline compound was filtered and dried to get pure scopoletin. The process of crystallization was repeated two times to get 40% of a purified compound. The remaining scopoletin in filtrate was isolated by column clromatography over silica gel in the ratio of (1:5) and the scopoletin was eluted with chloroform. The scopoletin containing fractions were evaporated and subjected to crystallization, which afforded pure scopoletin. Thereby (80%) of pure scopoletin was isolated from 100 gms of stem powder of 0.3% scopoletin content.

EXAMPLE 6
Extraction and isolation of scopoletin from leaves

*Artemisia annua* leaves were ground into powder. The powdered material (100 gm) was defatted with hexane (5×400 ml). After defatting the leaves the marc left was further extracted with 70% aqueous acetonitrile (5×500 ml) in a percolator for 6–8 hrs. The total extract was concentrated under a vacuum up to 30% of its original quantity. The concentrated aqueous extract was partitioned with chloroform (5×200 ml). The chloroform extract was dried over anhydrous sodium sulphate and the solvent was evaporated to get a 2.0 gm residue. The residue was redissolved in 25 ml methanol and kept for crystallization 4–5 hrs in a refrigerator. The crystalline compound was filtered and dried to get pure scopoletin. The process of crystallization was repeated two times to get 30% of a purified compound. The remaining scopoletin in filtrate was isolated by column chromatography over silica gel in the ratio of (1:20) and the scopoletin was eluted with 4% methanol in chloroform. The scopoletin containing fractions were evaporated and subjected to crystallization, which afforded pure scopoletin. Thereby (80%) of pure scopoletin was isolated from 100 gms of leaves powder of 0.23% scopoletin content.

The process for extraction and isolation of scopoletin, the subject matter of this patent, afforded number of advantages.

1. Acid base treatment method used for the isolation of total coumarins in prior arts is avoided in this process which can reduced the content of scopoletin.
2. The extraction with aqueous acetonitrile solvent is economic and higher yield of scopoletin than with other polar solvents like methanol,ethanol and water.
3. The amount of silica gel has reduced due to 50% of scopoletin crystallized before chromatography.
4. The process allowed the reuse of solvents
5. The selection of plant part stem for the extraction, improved the yield of scopoletin and reduced the cost of production because in *Artemisia annua* stems did not contain artemisinin and it is a waste material.
6. The high content of scopoletin in stem five times more stem biomass than leaves in Artemisia plant and less colouring material present in stem part yield easy purification.
7. The advantage are of significant economic value for large scale production of scopoletin from *Artemisia annua*.

What is claimed is:

1. A process for the isolation of the compound scopoletin from *Artemisia annua* and other plant families, said process comprising:

a) extracting dried powdered material of different plant parts with an aqueous acetonitrile solvent for 6 to 8 hours, wherein a ratio of the plant parts to the aqueous acetonitrile solvent is 1:5,
b) concentrating the extracted solvent up to 30% by volume of its original extract under vacuum,
c) partitioning the concentrated extract with halogenated solvent to transfer scopoletin in the non-polar halogenated solvent,
d) drying the halogenated solvent over anhydrous sodium sulphate and evaporating the solvent,
e) crystallizing residues from step (d) with a solvent and filtering the crystals to obtian a filtrate,
f) concentrating the filtrate,
g) subjecting the concentrated filtrate of step (f) to silica gel chromatography,
h) eluting scopoletin from the concentrated filtrate of step (g) in a chloroform/methanol mixture,
i) identifying the fractions containing the eluted scopolctin, and
j) crystallizing the fractions containing scopoletin to obtain a purified scopolctin compound.

2. A process as claimed in claim 1 wherein said other plant families are selected from the group consisting of Umbelliferae, Rutaceae, Compositae, Leguminosac, Moraceae, and Caryophyllacae.

3. A process as claimed in claim 1 wherein the plant parts used for extraction are selected from the group consisting of stems, leaves, and roots.

4. A process as claimed in claim 1 wherein a range of a ratio of acetonitrile to water in the aqueous acetonitrile solvent is 9:1 to 1:9.

5. A process claimed in claim 1 wherein the halogenated solvent is selected from the group consisting of chloroform, dichloromethane, and carbon tetrachloride.

6. A process claimed in claim 1 wherein the scopoletin is crystallized from the solvent, wherein the solvent is selected from the group consisting of chloroform, acetone, methanol and mixtures thereof.

7. A process claimed in claim 1, wherein said isolation yields scopoletin in a range of 0.25–0.30% from a stem, 0.16–0.20% from leaves, and 0.003–0.004% from roots.

8. A process as claimed in claim 1, wherein a ratio of the concentrated extract of step (g) to silica gel is the range of 1:5 to 1:20.

9. A process as claimed in claim 1, wherein a ratio of the concentrated extract of step (g) to silica gel is in the range of 1:5 to 1:10.

* * * * *